(12) United States Patent
Kurita et al.

(10) Patent No.: US 11,768,192 B2
(45) Date of Patent: Sep. 26, 2023

(54) CONDUCTIVE PARTICLE DETECTING DEVICE AND MECHANICAL DEVICE

(71) Applicant: Nabtesco Corporation, Tokyo (JP)

(72) Inventors: Masakazu Kurita, Tokyo (JP); Hiroki Mori, Tokyo (JP); Koji Nakamura, Tokyo (JP); Kazuhiko Sakurai, Tokyo (JP); Masaki Harada, Tokyo (JP)

(73) Assignee: NABTESCO CORPORATION, Tokyo (JP)

( * ) Notice: Subject to any disclaimer, the term of this patent is extended or adjusted under 35 U.S.C. 154(b) by 33 days.

(21) Appl. No.: 17/688,545

(22) Filed: Mar. 7, 2022

(65) Prior Publication Data

US 2022/0291188 A1   Sep. 15, 2022

(30) Foreign Application Priority Data

Mar. 12, 2021   (JP) ................................ 2021-040569

(51) Int. Cl.
    *G01N 33/28*     (2006.01)
    *G01N 27/07*     (2006.01)

(52) U.S. Cl.
    CPC ......... *G01N 33/2858* (2013.01); *G01N 27/07* (2013.01)

(58) Field of Classification Search
CPC ............... G01N 27/07; G01N 33/2858; G01N 15/0656; G01N 27/043; G01N 27/045; H05K 1/0277; H05K 1/18; H05K 2201/10053; H05K 2201/10151; H01F 7/02; F16H 57/0405
See application file for complete search history.

(56) References Cited

U.S. PATENT DOCUMENTS

| | | | | |
|---|---|---|---|---|
| 2012/0105057 | A1* | 5/2012 | Mol ....................... | G01D 5/145 324/251 |
| 2013/0050872 | A1* | 2/2013 | Sekii ..................... | H02K 1/146 310/71 |
| 2014/0021945 | A1* | 1/2014 | Omoto .................. | F16C 35/042 324/207.25 |
| 2019/0154608 | A1 | 5/2019 | Nakamura et al. | |

FOREIGN PATENT DOCUMENTS

| | | |
|---|---|---|
| EP | 3839504 A2 | 6/2021 |
| JP | 2005-331324 A | 12/2005 |

OTHER PUBLICATIONS

Extended European Search Report dated Jul. 15, 2022, issued in corresponding European Patent Application No. 22160777.3 (11 pgs.).

* cited by examiner

*Primary Examiner* — Giovanni Astacio-Oquendo
*Assistant Examiner* — Zannatul Ferdous
(74) *Attorney, Agent, or Firm* — Pillsbury Winthrop Shaw Pittman, LLP

(57) ABSTRACT

A conductive particle detecting device includes a plurality of electrodes, a permanent magnet, and a detecting circuit. The plurality of electrodes are arranged at intervals in a lubricant. The permanent magnet accumulates conductive particles in the lubricant between adjacent electrodes by a magnetic force. The detecting circuit detects target conductive particles based on electrical resistance between the adjacent electrodes. An attractive force of the permanent magnet acting on the conductive particles between the adjacent electrodes is set such that the lubricant remains as a non-conductive layer around fine-sized conductive particles having a smaller particle size than the target conductive particles.

10 Claims, 11 Drawing Sheets

CONDUCTIVE PARTICLE DETECTING DEVICE AND MECHANICAL DEVICE

CROSS-REFERENCE TO RELATED APPLICATIONS

This application is based on and claims the benefit of priority from Japanese Patent Application Serial No. 2021-040569 (filed on Mar. 12, 2021), the contents of which are hereby incorporated by reference in their entirety.

TECHNICAL FIELD

The present disclosure relates to a conductive particle detecting device and a mechanical device including the conductive particle detecting device.

BACKGROUND

In mechanical devices containing a mechanical mechanism (such as a speed reducer), a casing is filled with a lubricant to reduce the abrasion in the mechanism. In operation of such mechanical devices, abrasion and damage occur in the mechanical parts. The metal powder produced from the mechanical parts due to abrasion and damage mixes into the lubricant. When a large amount of metal powder mixes into the lubricant, the ability of the lubricant to inhibit the abrasion in the mechanism is reduced. The presence of the large amount of metal powder mixed into the lubricant indicates that the abrasion or damage has occurred in the mechanism.

Therefore, for the mechanical devices, it is desirable to externally detect that the amount of the metal powder mixing into the lubricant has exceeded a preset value. Devices for externally detecting the amount of the metal powder are disclosed (see, for example, Japanese Patent Application Publication No. 2005-331324 ("the '324 Publication")). With these devices, the metal powder in the lubricant is attracted by a permanent magnet, thereby electrically detecting the amount of the attracted metal powder.

The detecting device (the conductive particle detecting device) disclosed in the '324 Publication includes a tubular permanent magnet disposed in the lubricant and a plurality of electrodes disposed outside the permanent magnet and spaced apart from each other by a gap.

The conductive particle detecting device is configured to detect the resistance between adjacent electrodes spaced apart from each other by the gap, thereby determining the amount of metal powder mixing into the lubricant.

Typically, in a mechanical device, a large amount of fine initial abrasion powder (metal powder) is produced when machines are first operated. Therefore, as the mechanical device is operated for a long period, the lubricant contains not only fragments or metal powder produced by abrasion over time that should be detected (hereinafter referred to as "target metal powder"), but also the initial abrasion powder that hardly affects the operation of the mechanism.

Therefore, in the above conductive powder detecting device, the initial abrasion powder first accumulates between the electrodes spaced apart by the gap, and the target metal powder is adhered to the outer side of the accumulated initial abrasion powder. To securely detect the target metal powder that should be detected, the gap between the electrodes and the collection space of the metal powder has to be sufficiently large. However, when the gap between the electrodes and the collection space of the metal powder are sufficiently large, the size of the conductive particle detecting device is increased, and the degree of freedom in design is reduced.

SUMMARY

The present disclosure provides a conductive particle detecting device and a mechanical device capable of securely detecting the target conductive particles while inhibiting the increase in size and the reduction in degree of freedom in design.

(1) A conductive particle detecting device according to one aspect of the present disclosure comprises: a plurality of electrodes arranged at intervals in a non-conductive lubricant a permanent magnet for accumulating conductive particles between adjacent ones of the plurality of electrodes by a magnetic force, the conductive particles being a detection target mixing into the lubricant and a detecting circuit for detecting the conductive particles based on electrical resistance between the adjacent ones of the plurality of electrodes, wherein an attractive force of the permanent magnet is set such that the lubricant remains as a non-conductive layer around fine particles having electrical conductivity and having a smaller particle size than the conductive particles.

(2) The conductive particles have a particle size of 10 pia or larger, and the fine particles have a particle size of less than 10 μm.

(3) The fine particles preferably have a particle size of less than 2 μm.

(4) It is also possible that each of the plurality of electrodes has a primary surface to which the fine particles are adhered, and each of the plurality of electrodes includes a projection portion having electrical conductivity and partly projecting from the primary surface.

(5) The projection portion preferably includes a conductive non-magnetic material.

(6) The magnetic force of the permanent magnet is preferably set such that the fine particles adhered to each of the plurality of electrodes reach saturation within a range in which the fine particles do not entirely cover the projection portion, and the fine particles are dispersed in the lubricant.

(7) It is also possible that the magnetic force of the permanent magnet is set such that, in a mechanical device that produces a largest amount of conductive particles among a plurality of types of mechanical devices to which the conductive particle detecting device is applied, the fine particles adhered to each of the plurality of electrodes reach saturation within a range in which the fine particles do not entirely cover the projection portion, and the fine particles are dispersed in the lubricant.

(8) It is also possible that each of the plurality of electrodes includes: a body portion; and a projection member formed separately from the body portion and constituting the projection portion, and the projection member is pressed against the body portion by a detecting unit cover that covers a circumference of the body portion.

(9) A conductive particle detecting device according to another aspect of the present disclosure comprises: a plurality of permanent magnets having electrical conductivity arranged at intervals in a non-conductive lubricant; and a detecting circuit for detecting electrical resistance between electrodes different from each other, adjacent ones of the plurality of permanent magnets being defined as the electrodes different from each other, wherein conductive particles mixing into the lubricant are defined as a detection target, and particles having electrical conductivity and having a smaller particle size than the conductive particles are defined as fine particles, and wherein a part of the fine particles between the electrodes is maintained out of contact with the electrodes such that upon application of electric current, the fine particles do not conduct electricity to the electrodes.

(10) A conductive particle detecting device according to still another aspect of the present disclosure comprises: a plurality of electrodes arranged at intervals in a non-conductive lubricant a detecting circuit for detecting conductive particles based on electrical resistance between the plurality of electrodes, the conductive particles being a detection target mixing into the lubricant, wherein particles having electrical conductivity and having a smaller particle size than the conductive particles are defined as fine particles, and wherein upon application of electric current, the fine particles do not conduct electricity to the plurality of electrodes.

(11) A mechanical device according to an aspect of the preset disclosure comprises: a mechanical mechanism; a casing containing the mechanism and a non-conductive lubricant and a conductive particle detecting device for detecting conductive particles, the conductive particles being a detection target mixing into the lubricant, wherein the conductive particle detecting device includes: a plurality of electrodes arranged at intervals in the lubricant a permanent magnet for accumulating the conductive particles between adjacent ones of the plurality of electrodes by a magnetic force; and a detecting circuit for detecting the conductive particles based on electrical resistance between the adjacent ones of the plurality of electrodes, wherein an attractive force of the permanent magnet is set such that upon application of electric current, fine particles having electrical conductivity and having a smaller particle size than the conductive particles do not conduct electricity to the plurality of electrodes.

In the above conductive particle detecting devices, the lubricant between adjacent electrodes remains as a non-conductive layer around fine-sized conductive particles having a smaller particle size than the target conductive particles. Therefore, even when the initial abrasion powder formed of the fine-sized conductive particles accumulates between adjacent electrodes, the non-conductive layer around the initial abrasion powder prevents erroneous detection of the detecting circuit. Accordingly, with the above conductive particle detecting devices, it is possible to inhibit the expansion of the gap between the electrodes and the expansion of the collection space of the conductive particles, and thus it is possible to securely detect the target conductive particles while inhibiting the increase in size of the device and the reduction in degree of freedom in design.

DESCRIPTION OF THE EMBODIMENTS

The embodiments of the present disclosure will be hereinafter described with reference to the drawings. In the following embodiments, like elements will be denoted by the same reference signs and redundant descriptions will be partly omitted.

Figure 1:
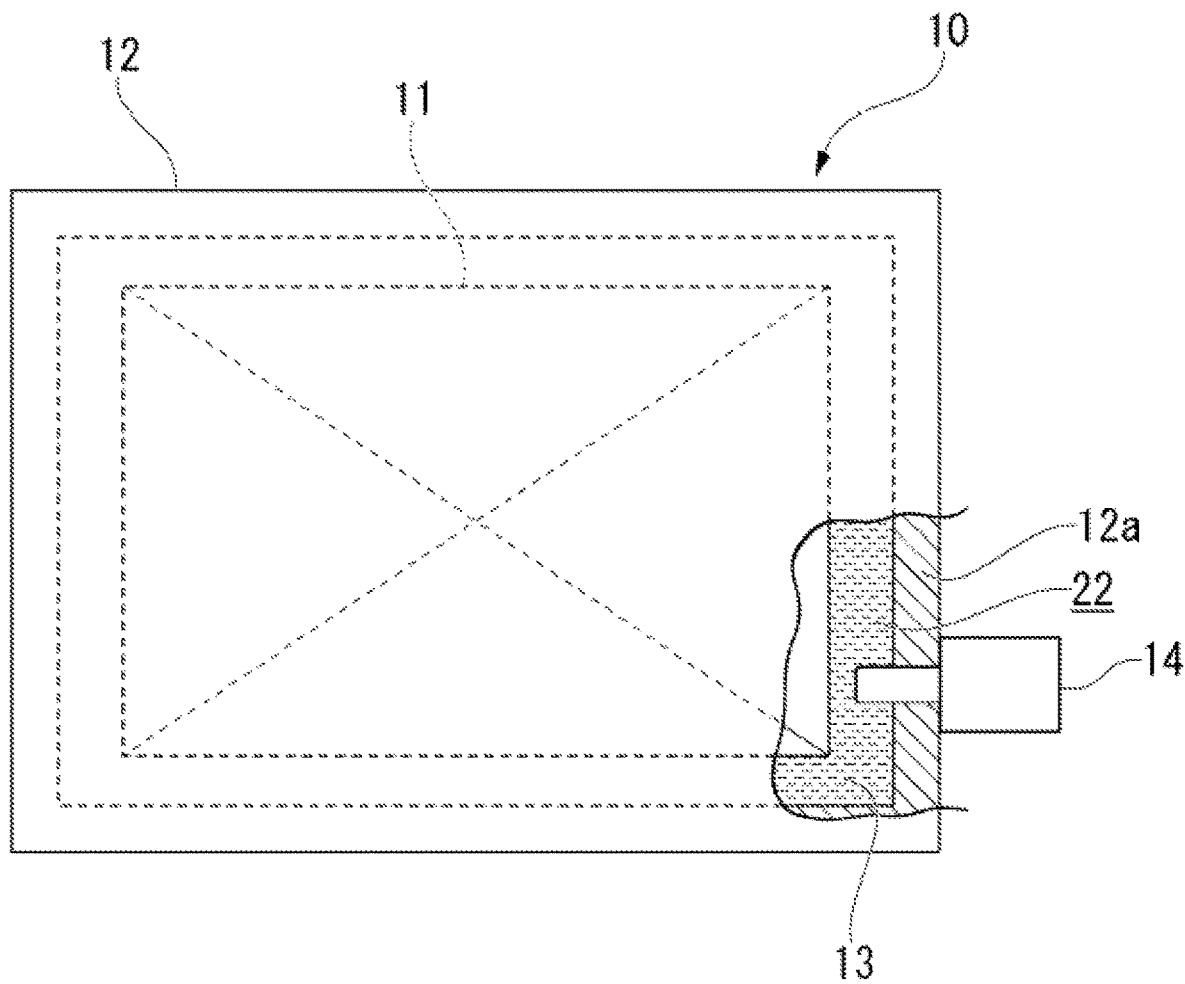
FIG. 1 is a partially sectional side view showing a speed reducer (mechanical device) according to an embodiment.

FIG. 1 is a partially sectional side view showing a speed reducer 10, which is a form of a mechanical device. The speed reducer 10 includes: a speed reducing mechanism unit 11 for decelerating input rotation to a predetermined reduction ratio; and a casing 12 that houses the speed reducing mechanism unit 11. The inner space within the casing 12 is filled with a lubricant 13 for lubricating the speed reducing mechanism unit 11 and other mechanical contact parts. A conductive particle detecting device 14 is mounted to a wall 12a of the casing 12. The conductive particle detecting device 14 detects conductive particles such as metal powder mixing into the lubricant 13. In the embodiment, the speed reducing mechanism unit 11 and the other mechanical contact parts constitute a mechanical mechanism disposed in the casing 12. The lubricant filled in the casing 12 is non-conductive.

Configuration of First Embodiment

Figure 2:
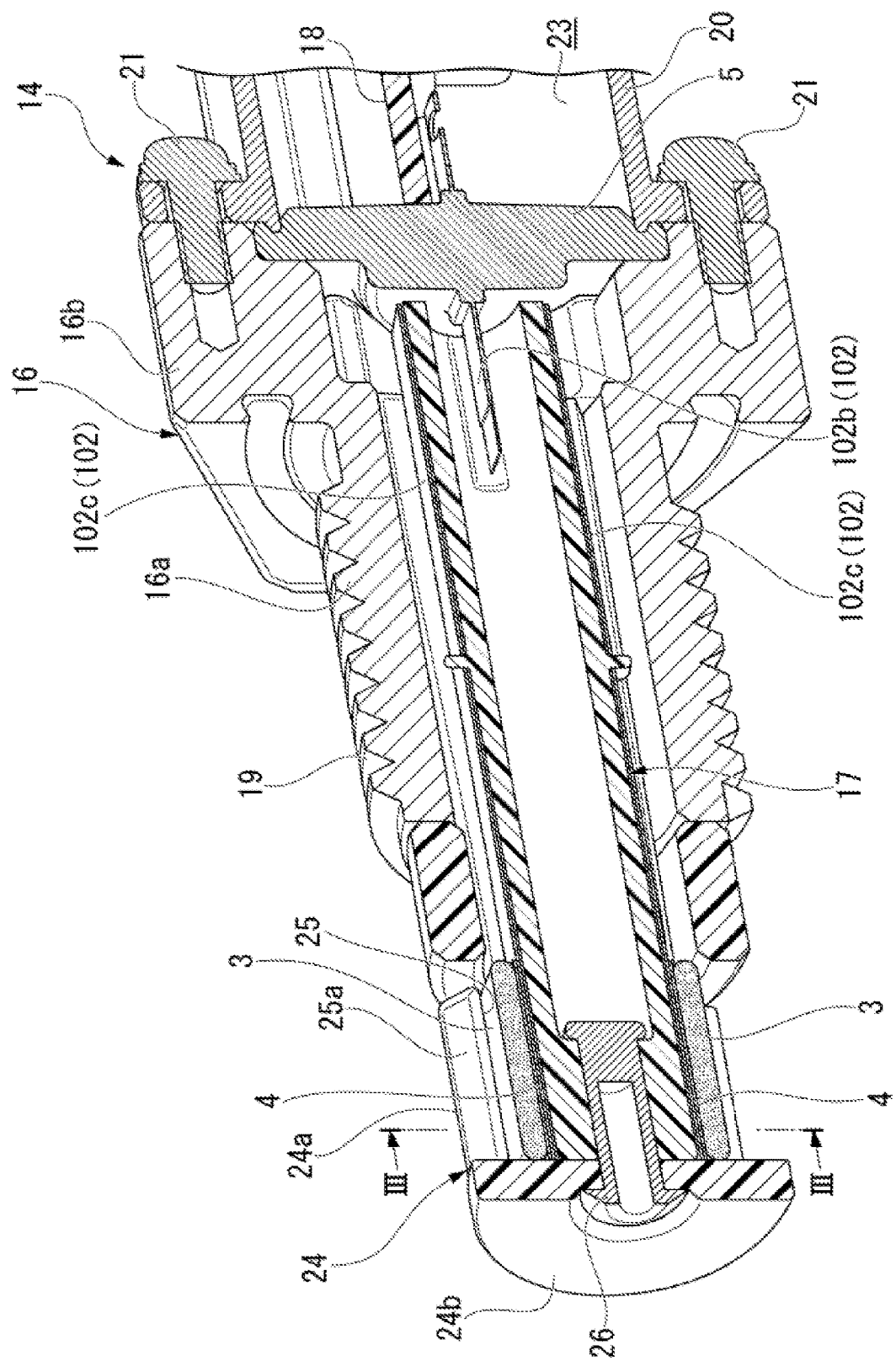
FIG. 2 is a partial sectional perspective view showing a conductive particle detecting device according to a first embodiment.
Figure 3:
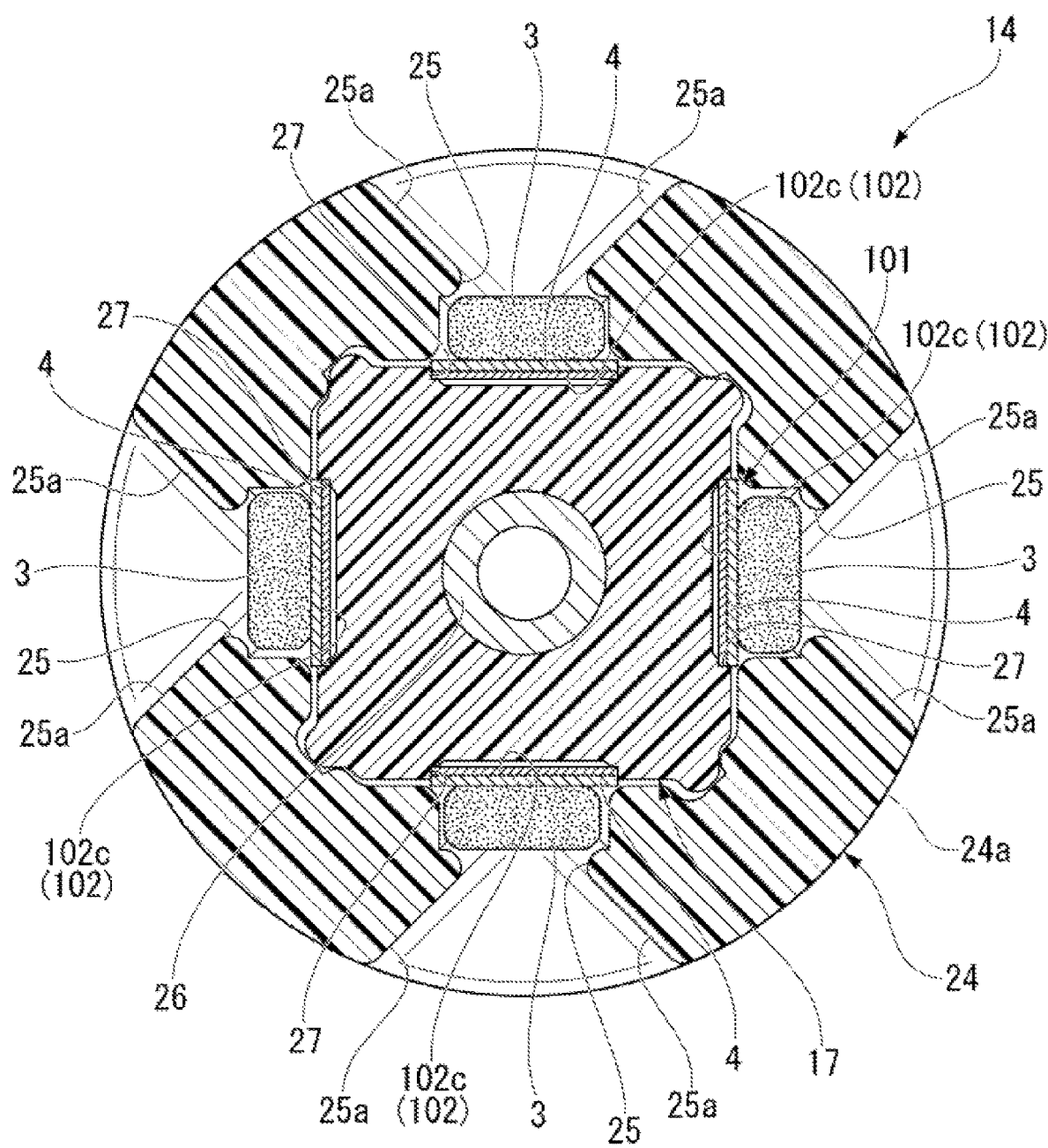
FIG. 3 is a sectional view along the line III-III in FIG. 2.

FIG. 2 is a perspective view showing a part of the conductive particle detecting device 14 longitudinally sectioned along the longitudinal direction. FIG. 3 is a sectional view along the line III-III in FIG. 2. The conductive particle detecting device 14 includes a device body 16 having a substantially tubular shape, a support block 17 fixed to the inside of the device body 16, and a flexible printed wiring board 102 (wiring) supported by the support block 17. The conductive particle detecting device 14 includes: four permanent magnets 3 connected via relay pieces 4 to one end portion of the flexible printed wiring board 102 in the longitudinal direction; and a detecting circuit board 18 connected to the other end portion of the flexible printed wiring board 102 in the longitudinal direction.

The device body 16 is mounted to the casing 12 (see FIG. 1) of the speed reducer 10. The wall 12a of the casing 12 has a screw hole penetrating the wall 12a. The device body 16 is formed of, for example, a metal. The device body 16 includes a fixed tube 16a having a cylindrical shape and a flange portion 16b. The fixed tube 16a is fastened into the screw hole formed in the wall 12a. Thus, the device body 16 is mounted to the casing 12 in such a manner as to penetrate the wall 12a. The flange portion 16b is integrated with an end portion of the fixed tube 16a (the end portion positioned outside the casing 12).

A male thread 19 is formed in the outer circumferential surface of the fixed tube 16a. The male thread 19 is fastened into the screw hole in the wall 12a. A device cover 20 having a bottomed tubular shape is provided outside the flange portion 16b. The device cover 20 is fixed with bolts 21 (fastening members) to an outside end surface of the flange portion 16b (the end surface facing toward the opposite side to the casing 12). A grommet 5 (sealing member) having a disc-like shape seals between the device cover 20 and the flange portion 16b. The grommet 5 is integrated with a part of an insulating layer of the flexible printed wiring board 102. The flexible printed wiring board 102 is integrated with the grommet 5 so as to penetrate the grommet 5 in the thickness direction thereof.

The detecting circuit board 18 is mounted to the outside end surface of the grommet 5 (the end surface facing toward the opposite side to the casing 12). The detecting circuit board 18 is covered by the device cover 20. The grommet 5 is fixed to the device cover 20 and the flange portion 16b, with the peripheral edge of the grommet 5 nipped between the device cover 20 and the flange portion 16b. The grommet 5 seals between a lubricant-filled space 22 (see FIG. 1) inside the casing 12 of the speed reducer 10 and a detection space 23 (the space inside the device cover 20) in which the detecting circuit board 18 is disposed.

The support block 17 is formed of a resin material and shaped like a hollow quadrangular prism. One end portion (hereinafter referred to as "the proximal portion") of the support block 17 in the longitudinal direction is fixed to the inside of the device body 16. The support block 17 is positioned along the axial direction of the fixed tube 16a. The other end portion (hereinafter referred to as "the distal end portion") of the support block 17 in the longitudinal direction projects out of the fixed tube 16a of the device body 16 (to the inside of the casing 12).

The outer peripheral surface and the distal end surface of the distal end portion of the support block 17 are covered by a detecting unit cover 24 having a bottomed tubular shape. The detecting unit cover 24 is integrally formed of a resin material. The detecting unit cover 24 includes a peripheral wall 24a and an end wall 24b. The peripheral wall 24a has four detection windows 25, and the end wall 24b closes the axial end portion of the peripheral wall 24a. The four detection windows 25 of the peripheral wall 24a are arranged at regular intervals and spaced apart from each other by about 90° in the outer periphery of the peripheral wall 24a. Each of the detection windows 25 has a substantially rectangular shape in front view. Of the edges constituting each detection window 25, those on both sides along the circumferential direction of the peripheral wall 24a are formed in tapered surfaces 25a. The tapered surfaces 25a are formed such that the opening area of the detection window 25 increases gradually radially outward.

The end wall 24b of the detecting unit cover 24 is riveted to the distal end surface of the support block 17. The sign 26 in the drawing denotes a rivet for fixing the detecting unit cover 24 to the support block 17.

As shown in FIG. 2, the flexible printed wiring board 102 includes a base portion 102b and branch portions 102c branched from the base portion 102b in four directions. The base portion 102b penetrates the grommet 5 in the thickness direction thereof. Each of the four branch portions 102c is positioned along associated one of the four surfaces on the outer periphery of the support block 17. Support grooves 27 (see FIG. 3) are formed in the four surfaces on the outer periphery of the support block 17 so as to extend along the longitudinal direction of the support block 17. In each surface of the support block 17, the branch portion 102c is supported in the support groove 27.

The distal end portion of each branch portions 102c constitutes a terminal portion (conductive portion). Each terminal portion is connected with a respective relay piece 4. The relay piece 4 is formed of a metal magnetic material and substantially shaped like a rectangular plate. The relay piece 4 is connected to the terminal portion with a conductive adhesive or by soldering or by any other means. On the distal end portion of the support block 17, each relay piece 4 is supported in the associated support groove 27 along with the branch portion 102c. The surface of each relay piece 4 facing the opposite side to the support block 17 (hereinafter referred to as "the surface") is formed flat. The surface of each relay piece 4 has the associated permanent magnet 3 fixed thereto by magnetic attraction. Each permanent magnet 3 has electrical conductivity. The permanent magnet 3 is connected to a power supply (not shown) through the flexible printed wiring board 102 and the detecting circuit board 18. In the embodiment, the plurality of permanent magnets 3 adjacent to each other on the outer periphery of the support block 17 are connected to the power supply and thus form electrodes for detecting resistance. It is also possible to provide electrodes separately from the permanent magnets 3.

After the relay piece 4 and the permanent magnet 3 are mounted to each surface of the support block 17, the detecting unit cover 24 is mounted to the distal end portion of the support block 17. The detecting unit cover 24 is positioned such that each of the four permanent magnets 3 is positioned on the inner side of the associated one of the four detection windows 25 (on the inner side in the radial direction of the peripheral wall 24a). In this state, the detecting unit cover 24 is riveted to the distal end surface of the support block 17. At this time, the end surface of the peripheral wall 24a of the detecting unit cover 24 (the end surface on the opposite side to the end wall 24b) abuts against the end surface of the fixed tube 16a of the device body 16.

The distal end portion of the conductive particle detecting device 14 is inserted into the casing 12 through the screw hole in the wall 12a. In this state, the fixed tube 16a of the conductive particle detecting device 14 is fastened into the screw hole. Thus, the conductive particle detecting device 14 is fixed to the casing 12. The lubricant 13 is then filled into the casing 12, and the plurality of permanent magnets 3 and the detecting unit cover 24 are immersed in the lubricant 13.

The detecting circuit board 18 includes a detecting circuit. The detecting circuit of the detecting circuit board 18 detects the electrical resistance between the plurality of permanent magnets 3 arranged adjacent to each other on the outer periphery of the support block 17. As shown in FIG. 3, the plurality of permanent magnets 3 are spaced apart from each other. Therefore, in the initial state in which the permanent magnets 3 are immersed in the lubricant 13, the resistance value between adjacent permanent magnets 3 is infinite. After that, when a large amount of metal powder (conductive particles) mixes into the lubricant 13 as the speed reducer 10 is used, the metal powder in the lubricant 13 are attracted by the plurality of permanent magnets 3. The metal powder attracted in this way is moved through the detection windows 25 of the detecting unit cover 24 and attached onto the surfaces of the permanent magnets 3. Also, the metal powder attracted is attached onto the outer peripheral surface of the detecting unit cover 24 by the magnetic force of the permanent magnets 3.

As a larger amount of metal powder mixes into the lubricant 13, a larger amount of metal powder is also attached onto the outer peripheral surface of the detecting unit cover 24. When the amount of metal powder attached exceeds a certain amount, the resistance value between adjacent ones of the permanent magnets 3 falls below a preset value. The detecting circuit board 18 detects that the resistance value has fallen below the preset value. The detecting circuit board 18 is connected to a display device or an alarm device via a controller. Through the display device or the alarm device, an operator and the like can determine that the amount of metal powder in the speed reducer 10 has exceeded the preset amount.

The attractive force of the permanent magnets 3 acting on the metal powder is determined by the magnetic force of the permanent magnets 3 and the distance between adjacent ones of the permanent magnets 3 on the detecting unit cover 24. The attractive force of the permanent magnets 3 acting on the metal powder is also impacted by factors such as the viscosity of the lubricant 13. In the conductive particle detecting device 14 of the embodiment, the above factors are adjusted to satisfy Condition (a) below, thereby setting the attractive force acting on the metal powder. Condition (a): the lubricant 13 remains as a non-conductive layer around fine-sized metal powder (fine particles) having a smaller particle size than the target metal powder (conductive particles). The phrase "target metal powder" in Condition (a) refers to abrasion powder or fragments of mechanical parts produced by normal operation. The particle size of the "target metal powder" is 10 μm or larger, or preferably, 20 μm or larger. The phrase "fine-sized metal powder" in Condition (a) refers to initial abrasion powder produced when the speed reducer 10 is first operated. The particle size of the "fine-sized metal powder" is less than 10 μm, or preferably, less than 2 μm.

Figure 4A:
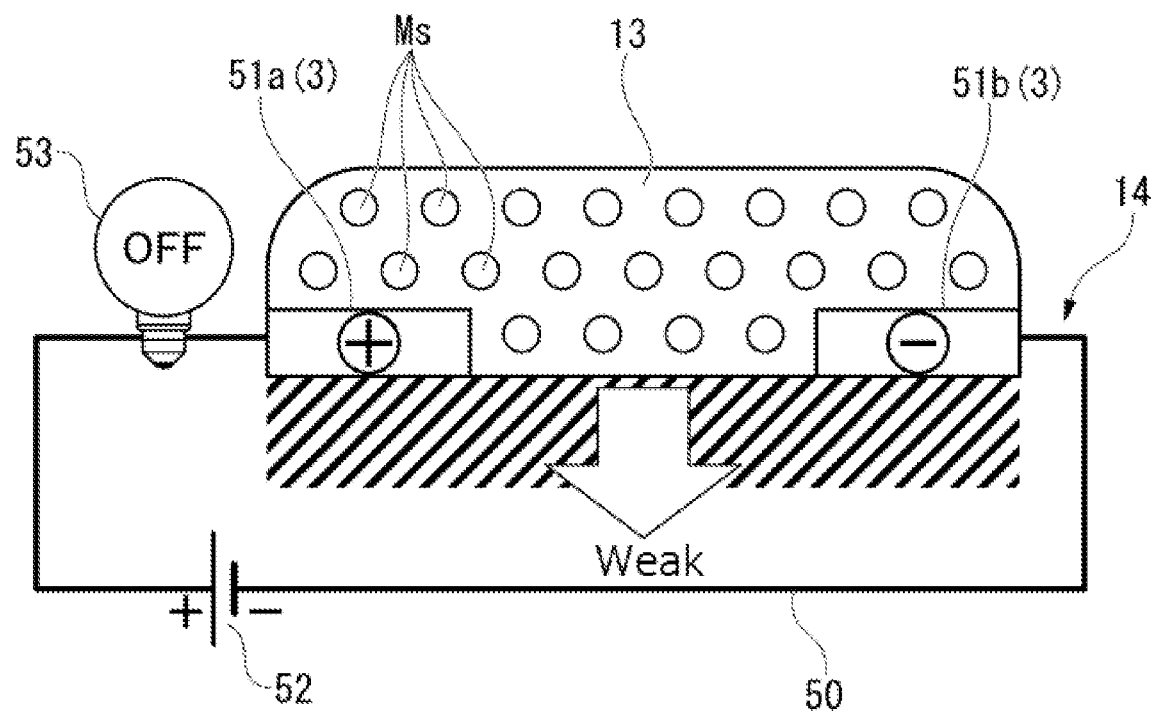
FIG. 4A is a schematic sectional view showing functionality of the conductive particle detecting device according to the first embodiment.
Figure 4B:
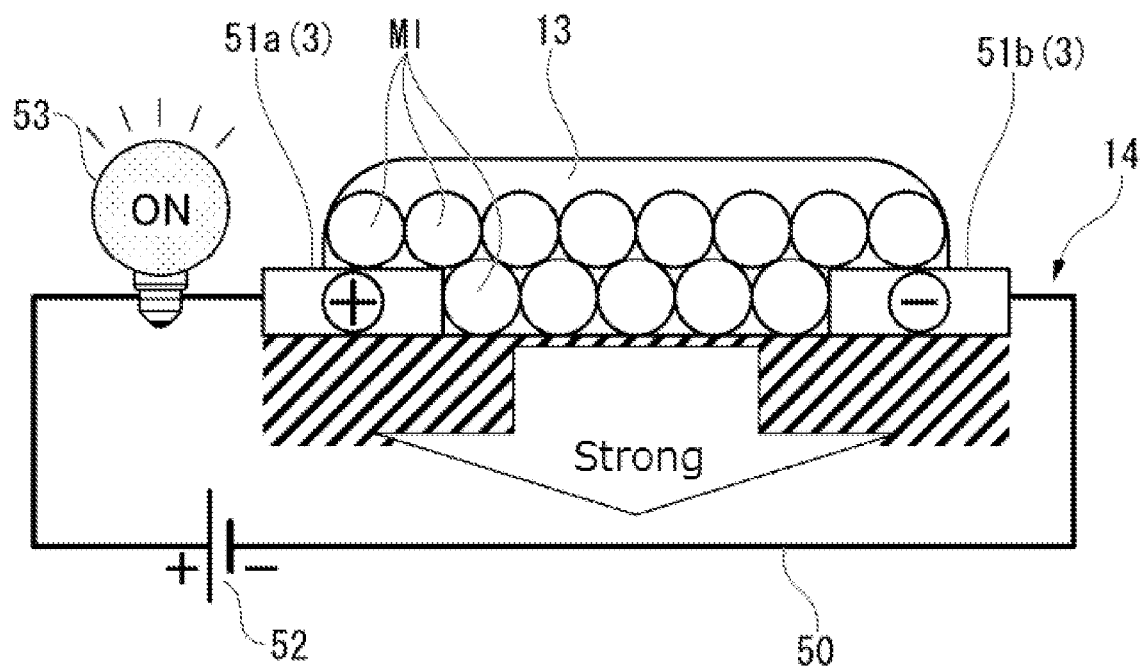
FIG. 4B is a schematic sectional view showing functionality of the conductive particle detecting device according to the first embodiment.

FIGS. 4A and 4B are schematic sectional views of the conductive particle detecting device 14 showing functionality of the conductive particle detecting device 14. FIG. 4A shows that the conductive particle detecting device 14 is attracting fine-sized metal powder Ms (initial abrasion powder). FIG. 4B shows that the conductive particle detecting device 14 is attracting target metal powder Ml (abrasion powder other than the initial abrasion powder, including the fragments). The sign 50 in FIGS. 4A and 4B denotes a detecting circuit for detecting an electrical resistance between two electrodes 51a, 51b (permanent magnets 3) adjacent to each other. The sign 52 denotes a power supply. The sign 53 denotes a resistance detecting unit in the detecting circuit 50. The word "OFF" placed within the resistance detecting unit 53 in FIG. 4A indicates that the detected resistance is larger than a preset value and thus no target metal powder Ml is detected. The word "ON" placed within the resistance detecting unit 53 in FIG. 4B indicates that the detected resistance is equal to or less than the preset value and thus the target metal powder Ml is detected.

In the conductive particle detecting device 14 of the embodiment, the attractive force of the permanent magnets 3 acting on the metal powder is adjusted to satisfy Condition (a) above. Therefore, as shown in FIG. 4A, the lubricant 13 remains as a non-conductive layer around the fine-sized metal powder Ms. Thus, even when the fine-sized metal powder Ms is attracted and accumulated between the two electrodes 51a, 51b adjacent to each other, particles of the metal powder Ms are in non-conductive state, and therefore, the resistance value between the two electrodes 51a, 51b does not fall below the preset value (the metal powder Ms is not detected erroneously as the target metal powder Ml). The phrase "non-conductive state" includes the state in which a part of the metal powder Ms is maintained out of contact with the electrodes 51a, 51b such that upon application of the electric current, the metal powder Ms does not conduct electricity to the electrodes 51a, 51b.

Figure 5:
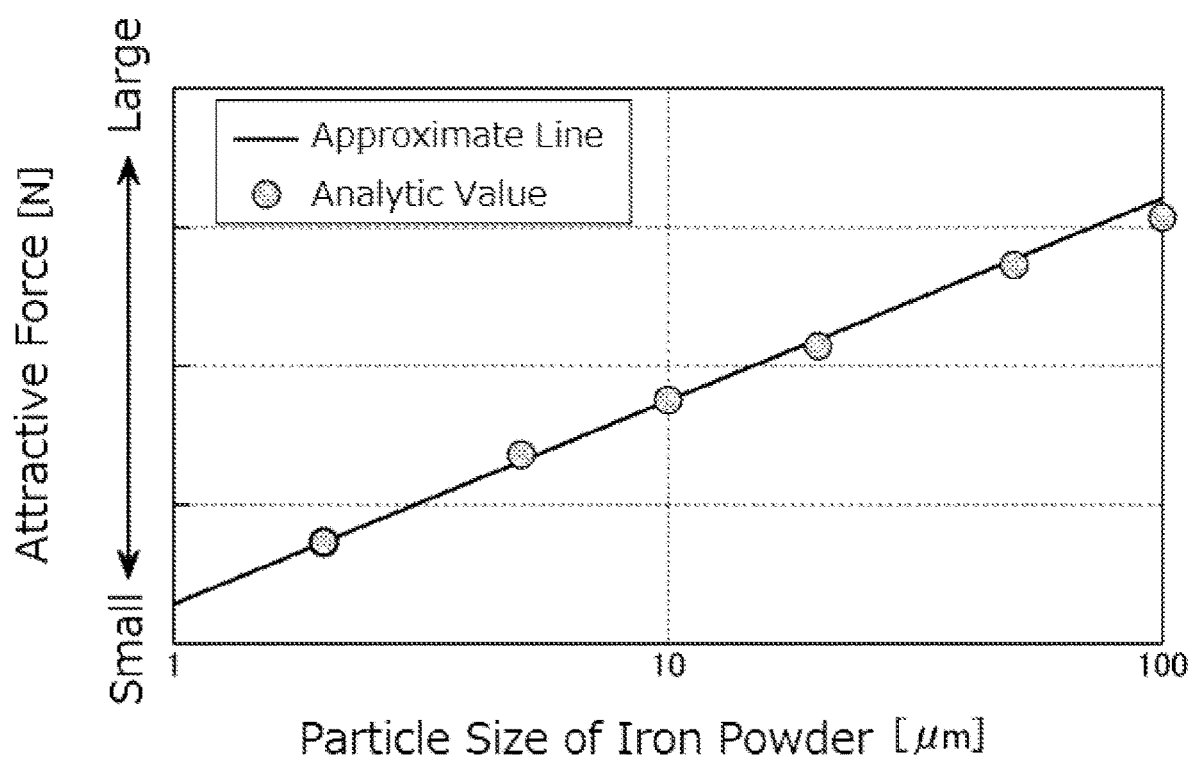
FIG. 5 is a graph showing a relationship between the particle size of iron powder and the attractive force of a permanent magnet.

In the conductive particle detecting device 14 of the embodiment, the attractive force of the permanent magnets 3 acting on the metal powder is adjusted to satisfy Condition (a) above. Therefore, as shown in FIG. 4B, the circumference of each particle of the target metal powder Ml is not entirely or completely covered by the lubricant 13. FIG. 5 is a graph showing a relationship between the particle size of iron powder (particle size of the metal powder) and the attractive force of the permanent magnets 3. As shown in the graph of FIG. 5, the metal powder (iron powder) receives a larger attractive force from the permanent magnets 3 as the particle size is larger. The metal powder having a particle size of 10 μm or larger receives an extremely larger attractive force than the metal powder having a particle size of less than 10 μm (in particular, the metal powder having a particle size of less than 2 μm). Therefore, the target metal powder Ml receives a large attractive force from the permanent magnets 3. As a result, the particles of the target metal powder Ml push the films of the lubricant 13 aside and directly contact with each other. When the target metal powder Ml is attracted and accumulated between the two electrodes 51a, 51b adjacent to each other, the particles of the metal powder Ml enter the conductive state. The resistance value between the two electrodes 51a, 51b falls below the preset value (the target metal powder Ml is detected).

The initial abrasion powder produced when the speed reducer 10, which is a mechanical device, is first operated is fine metal powder (fine-sized metal powder Ms) having a particle size of less than 10 μm (normally less than 2 μm). The initial abrasion powder is produced in the initial period after the start of service of the speed reducer 10. Therefore, in the initial stage of service, the initial abrasion powder is adhered to the surfaces of the electrodes 51a, 51b and the detecting unit cover 24 (see FIGS. 2 and 3) of the conductive particle detecting device 14. As a result, the initial abrasion powder forms a lower layer of an accumulation layer accumulated on the electrodes 51a, 51b and the detecting unit cover 24 of the conductive particle detecting device 14. The metal powder such as the abrasion powder and the fragments produced during normal operation of the speed reducer 10 (the target metal powder) is naturally adhered onto the initial abrasion powder. As a result, the target metal powder Ml forms the upper layer of the accumulation layer. Although the target metal powder Ml is accumulated on the initial abrasion powder, the target metal powder Ml has a large particle size and receives a large attractive force from the permanent magnets 3, and thus the target metal powder Ml is securely attracted over the initial abrasion powder. Accordingly, the target metal powder Ml produced in the speed reducer 10 is securely detected by the conductive particle detecting device 14.

Advantageous Effects of First Embodiment

As described above, in the conductive particle detecting device 14 of the embodiment, the attractive force of the permanent magnets 3 is set such that the lubricant 13 remains as a non-conductive layer around the fine-sized metal powder Ms (the metal powder having a particle size of less than 10 μm) having a smaller particle size than the target metal powder Ml (the metal powder having a particle size of 10 μm or larger). Therefore, in the detection gap between the electrodes 51a, 51b adjacent to each other, the lubricant remains as a non-conductive layer around the initial abrasion powder, which is the fine-sized metal powder (the metal powder having a particle size of less than 10 μm). As a result, even when more than a preset amount of initial abrasion powder is accumulated in the detection gap between the electrodes 51a, 51b adjacent to each other, the initial abrasion powder is not detected as the target abrasion powder Ml by the detecting circuit 50. Since the attractive force acting on the initial abrasion powder is relatively weak, a small amount of initial abrasion powder accumulates in the detection gap between the electrodes 51a, 51b. Therefore, with the conductive particle detecting device 14 of the embodiment, it is possible to inhibit the expansion of the detection gap between the electrodes 51a, 51b and the expansion of the collection space of the metal powder. As a result, it is possible to securely detect the target metal powder Ml, while inhibiting the increase in size of the device and the reduction in degree of freedom in design.

Configuration of Second Embodiment

Figure 6A:
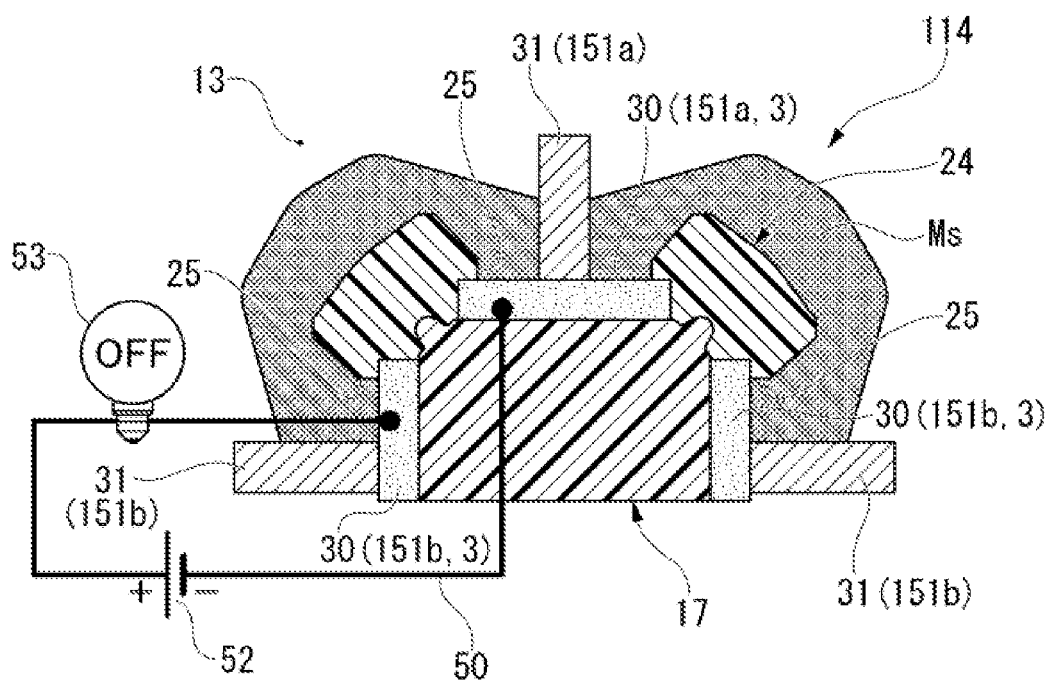
FIG. 6A is a schematic sectional view showing a conductive particle detecting device according to a second embodiment.
Figure 6B:
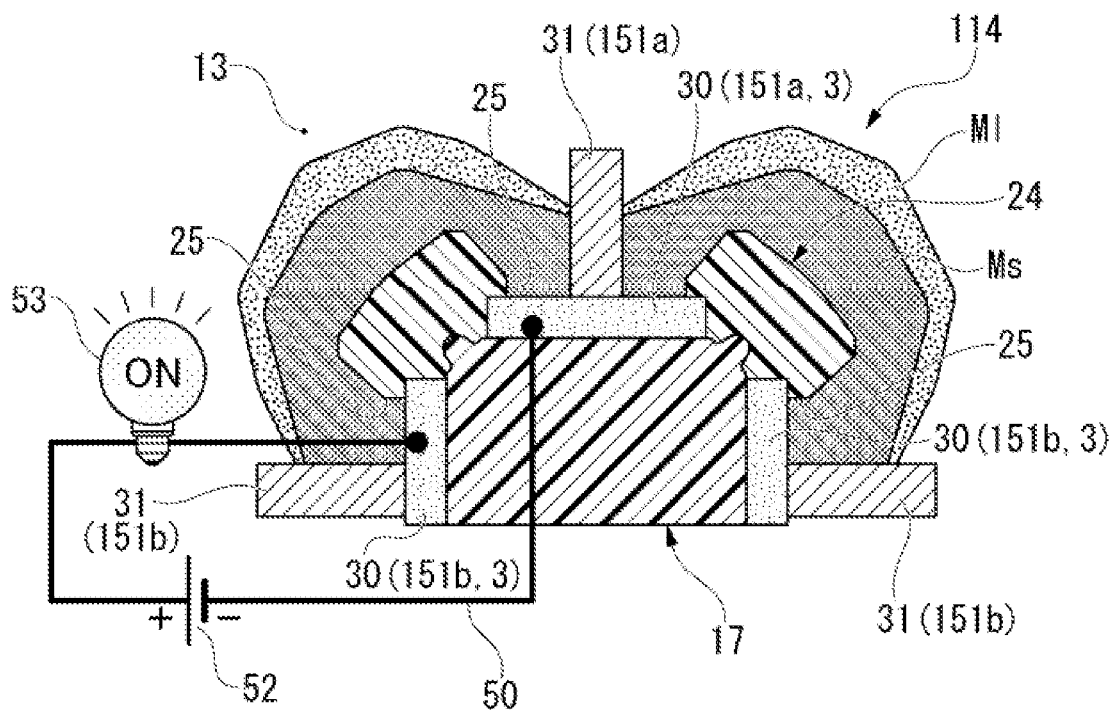
FIG. 6B is a schematic sectional view showing the conductive particle detecting device according to the second embodiment.

FIGS. 6A and 6B are schematic sectional views showing functionality of the conductive particle detecting device 114 according to the present embodiment. FIG. 6A shows that the conductive particle detecting device 114 has attracted the fine-sized metal powder Ms (initial abrasion powder) in the initial period after the start of service of the speed reducer 10. FIG. 6B shows that thereafter the conductive particle detecting device 114 has attracted the target metal powder Ml. The conductive particle detecting device 114 of the embodiment is basically configured in the same manner as in the first embodiment. However, electrodes 151a, 151b are configured in a different manner than in the first embodiment.

Each of the electrodes 151a, 151b includes a body portion 30 and a projection member 31 (projection portion). The body portion 30 is formed of a conductive permanent magnet 3, and the projection member 31 (projection portion) has electrical conductivity and is mounted to the body portion 30 in a contacting manner. The electrodes 151a, 151b have the same structure except that they have different polarities. The body portion 30 has a substantially rectangular shape. As with the electrodes 51a, 51b of the first embodiment, the body portion 30 is disposed within the detection window 25 of the detecting unit cover 24. The flat surface of the body portion 30 (the surface facing radially outward) faces the outside (the space filled with the lubricant 13) through the detection window 25. The body portion 30 of each of the electrodes 151a, 151b is electrically connected with the power supply 52 and the resistance detecting unit 53 of the detecting circuit 50.

The projection member 31 is fixed by, for example, a conductive adhesive to the surface (hereinafter referred to as "the primary surface") of the body portion 30 facing the outside (the space filled with the lubricant). The projection member 31 projects toward the outside from a part of the primary surface of the body portion 30. The cross section of the projection member 31 along the direction orthogonal to the projecting direction is sufficiently smaller than the primary surface of the body portion 30. The projection member 31 of the embodiment is formed of a conductive non-magnetic material such as brass, aluminum, or copper. Therefore, the projection member 31 itself does not attract the metal powder, although it is contacted with the body portion 30 formed of the permanent magnet 3.

The magnetic force of the permanent magnet 3 constituting the body portion 30 is set such that the fine-sized metal powder Ms (initial abrasion powder) adhered to the electrodes 151a, 151b reaches saturation within a range in which the projection member 31 is not entirely covered, and the fine-sized metal powder (fine particles) Ms is dispersed in the lubricant 13. Therefore, as shown in FIG. 6A, when the fine-sized metal powder Ms in the lubricant 13 accumulates between the electrodes 151a, 151b adjacent to each other, the restraint of new metal powder Ms by the magnetic force is stopped before the accumulated metal powder Ms covers the entirety of the projection member 31. As a result, new metal powder Ms is dispersed in the lubricant.

For the conductive particle detecting device 14 of the embodiment, the attractive force on the metal powder acting between the plurality of permanent magnets 3 (the electrodes 151a, 151b) adjacent to each other is also set so as to satisfy Condition (a) described for the first embodiment. Therefore, the lubricant 13 remains as a non-conductive layer around the fine-sized metal powder Ms (the initial abrasion powder) accumulated between the electrodes 151a, 151b adjacent to each other. Accordingly, as shown in FIG. 6A, when only the fine-sized metal powder Ms (the initial abrasion powder) is accumulated between the electrodes 151a, 151b adjacent to each other, the electrical resistance between the electrodes 151a, 151b adjacent to each other does not fall below the preset value. Therefore, the resistance detecting unit 53 does not erroneously detect that more than the preset amount of the target metal powder Ml has been produced.

As shown in FIG. 6B, when the accumulation of the initial abrasion powder (the fine-sized metal powder Ms) is ended, and the target metal powder Ml is accumulated to some degree between the electrodes 151a, 151b adjacent to each other, the target metal powder Ml conducts electricity between the electrodes 151a, 151b. As a result, the electrical resistance between the electrodes 151a, 151b falls below the preset value, and the resistance detecting unit 53 detects that the target metal powder Ml has been produced Since the projection member 31 of each of the electrodes 151a, 151b is at least partly projecting to the outside of the initial abrasion powder (the fine-sized metal powder Ms), the presence of the target metal powder Ml can be securely detected.

Advantageous Effects of Second Embodiment

As described above, the conductive particle detecting device 114 of the embodiment, which is basically configured in the same manner as in the first embodiment, can produce substantially the same basic effects as the conductive particle detecting device 14 of the first embodiment.

In the conductive particle detecting device 114 of the embodiment, the conductive projection member 31 (projection portion) is mounted to the primary surface of the body portion 30 of each of the electrodes 151a, 151b onto which the fine-sized metal powder Ms (initial abrasion powder) is adhered and accumulated, and the conductive projection member 31 (projection portion) projects outward from the primary surface. Therefore, even when the fine-sized metal powder Ms (initial abrasion powder) is adhered and accumulated to some degree onto the primary surface of the body portion 30, at least a part of the projection member 31 projects to the outside of the accumulated metal powder Ms (initial abrasion powder). Accordingly, with the conductive particle detecting device 114 of the embodiment, it can be previously inhibited that the conductive portions of the electrodes 151a, 151b are entirely buried in the fine-sized metal powder Ms (initial abrasion powder), such that the detecting circuit 50 cannot detect that the target metal powder (the metal powder having a particle size of 10 µm or larger) is adhered. In the above embodiment, the projection member 31, which is a separate member, is mounted to the body portion 30. It is also possible that the projection portion projecting from the primary surface of each of the electrodes 151a, 151b is integrally formed of the same permanent magnet 3.

In the conductive particle detecting device 114 of the embodiment, the projection member 31 separate from the body portion 30 is formed of a non-magnetic conductor, and thus the projection member 31 is not magnetized by the magnetic force of the body portion 30 (permanent magnet). Therefore, it can be inhibited that the fine-sized metal powder Ms (initial abrasion powder) is adhered to the projection member 31. Accordingly, with the conductive particle detecting device 114 of the embodiment, it can be more securely inhibited that the projection member 31 is buried in the fine-sized metal powder Ms (initial abrasion powder), such that the detecting circuit 50 cannot detect that the target metal powder M1 (the metal powder having a particle size of 10 µm or larger) is adhered.

In the conductive particle detecting device 114 of the embodiment, the magnetic force of the permanent magnet 3 is set such that the fine-sized metal powder Ms (initial abrasion powder) adhered to the electrodes 151a, 151b reaches saturation within a range in which the projection member 31 is not entirely covered, and the fine-sized metal powder Ms is dispersed in the lubricant 13. Therefore, it can be more securely inhibited that the conductive portions of the electrodes 151a, 151b are entirely buried in the initial abrasion powder, such that the detecting circuit 50 cannot detect that the target metal powder M1 is adhered.

When the conductive particle detecting device 114 of the embodiment is used for a plurality of types of speed reducers 10 (mechanical devices) having different specifications, the magnetic force of the permanent magnet 3 is preferably set such that, in the speed reducer 10 that produces the largest amount of metal powder among the plurality of types of speed reducers 10, the fine-sized metal powder Ms (initial abrasion powder) reaches saturation within a range in which the projection member 31 is not entirely covered. In this case, a common conductive particle detecting device 114 can be used, without modification, for all the speed reducers 10 (mechanical devices), and there is no need of changing the setting such as the magnetic force of the permanent magnet 3. In other words, with the setting for preventing the projection member 31 from being buried in the fine-sized metal powder Ms (initial abrasion powder) in the speed reducer 10 (mechanical device) specified such that the largest amount of metal powder is adhered, the projection member 31 will not be buried in the fine-sized metal powder Ms (initial abrasion powder) in the speed reducers 10 (mechanical devices) specified otherwise such that a smaller amount of metal powder is adhered. Accordingly, with this configuration, a common conductive particle detecting device 114 can be used, without modification, for speed reducers 10 (mechanical devices) having different specifications, and thus the conductive particle detecting device 114 can be produced efficiently.

Configuration of Third Embodiment

Figure 7:
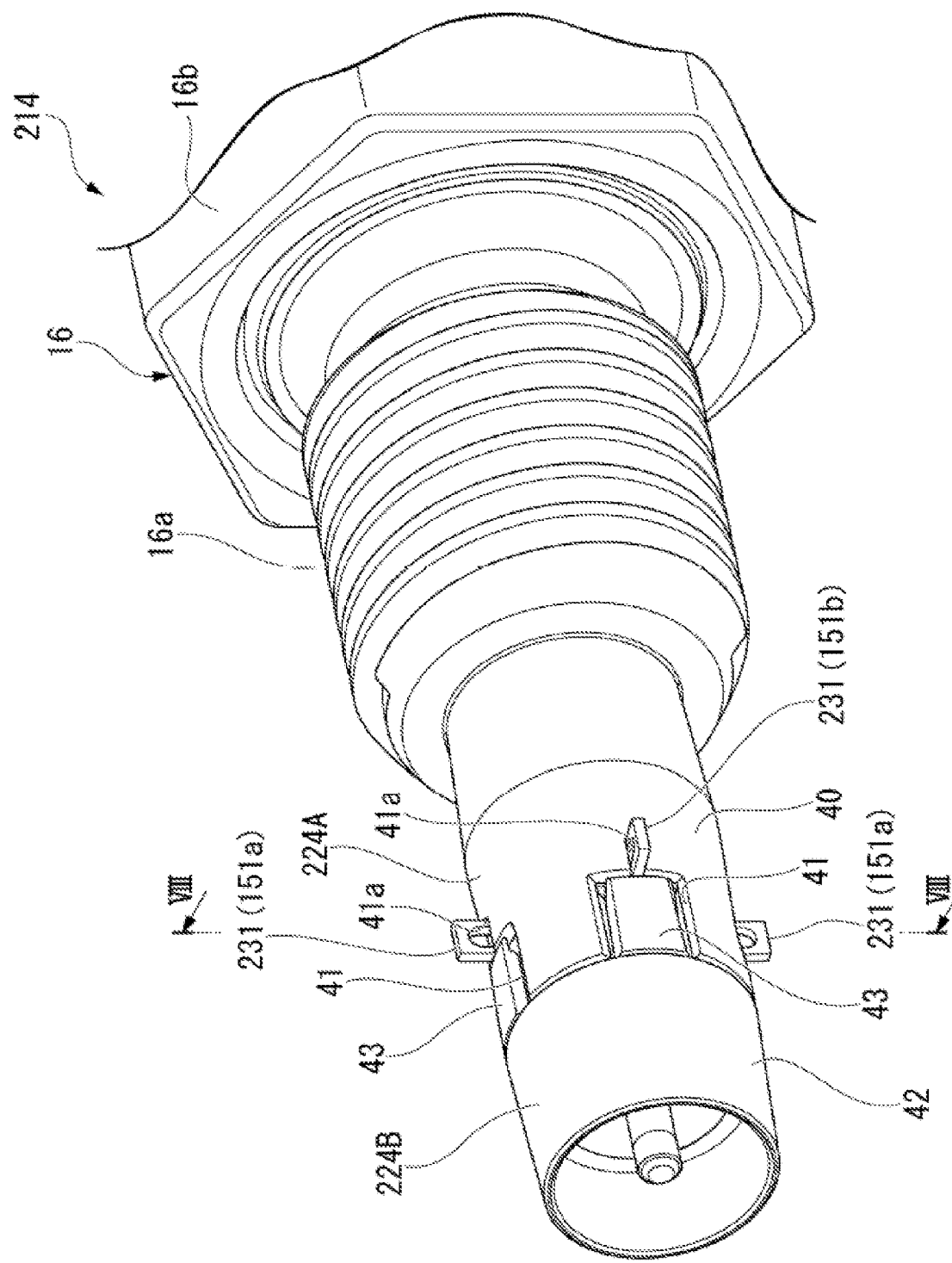
FIG. 7 is a perspective view showing a conductive particle detecting device according to a third embodiment.
Figure 8:
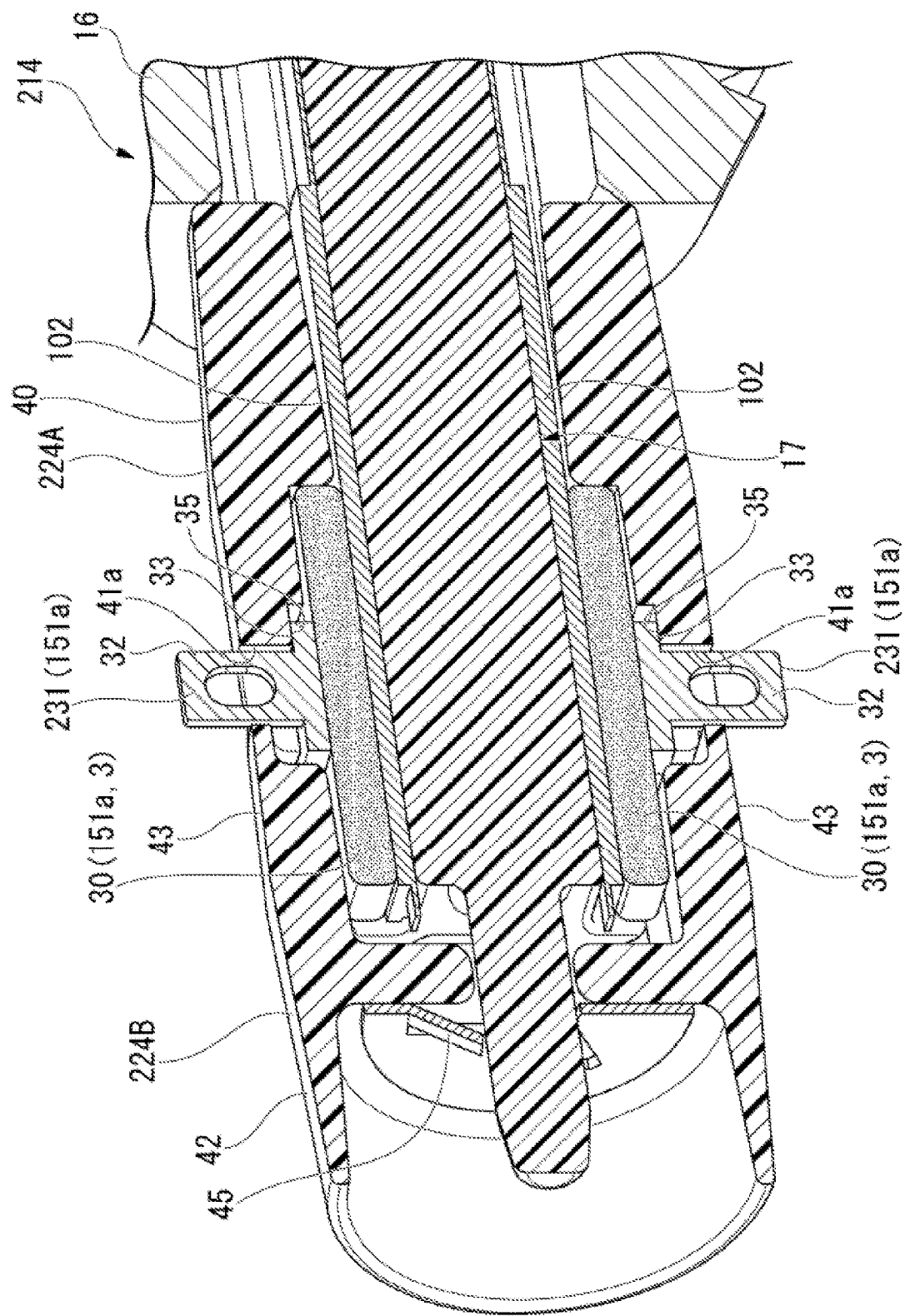
FIG. 8 is a partial sectional perspective view showing the conductive particle detecting device of FIG. 7 cut along the line VIII-VIII in FIG. 7.

FIG. 7 is a perspective view showing a conductive particle detecting device 214 according to the present embodiment. FIG. 8 is a partial sectional perspective view showing the conductive particle detecting device 214 of FIG. 7 cut along the line VIII-VIII. The conductive particle detecting device 214 of the embodiment is basically configured in substantially the same manner as in the second embodiment. The differences from the second embodiment are the shape of projection members 131 forming a part of the electrodes 151a, 151b and the way of placing (the way of fixing) the projection members 131.

Each of the electrodes 151a, 151b includes a body portion 30 and a projection member 231 (projection portion). The body portion 30 is formed of a permanent magnet 3 and shaped like a rectangular plate, and the projection member 231 (projection portion) is in contact with the primary surface (the surface facing outward) of the body portion 30. The projection member 231 is formed of a conductive non-magnetic material such as brass, aluminum, or copper. The projection member 231 includes an extension portion 32 and a flange portion 33. The extension portion 32 is shaped like a rectangular plate having a uniform width, and the flange portion 33 is provided on one end portion (hereinafter referred to as "the proximal portion" of the extension portion 32 in the extension direction orthogonal to the width direction of the extension portion 32. The projection member 231 is disposed such that the width direction of the extension portion 32 is along the axial direction of the support block 17. The end surface of the flange portion 33 is in contact with the primary surface of the body portion 30.

In the embodiment, a detecting unit cover formed of a resin is mounted to the outer periphery of the distal end side of the support block 17. The detecting unit cover includes a first detecting unit cover 224A on the proximal side and a second detecting unit cover 224B on the distal end side. Both the first detecting unit cover 224A and the second detecting unit cover 224B have a cylindrical shape. The first detecting unit cover 224A and the second detecting unit cover 224B are mounted to the support block 17 so as to cover the outer periphery of the support block 17.

In the peripheral wall 40 of the first detecting unit cover 224A, the edge portion on the distal end side (the side facing the second detecting unit cover 224B) has four cutouts 41 formed therein. Each of the cutouts 41 has a rectangular shape. The cutouts 41 are arranged at regular intervals in the circumferential direction of the peripheral wall 40. The cutouts 41 are positioned to substantially overlap the four permanent magnets 3 (the four body portions 30 of the electrodes 151a, 151b). At the bottom of each cutout 41 in the peripheral wall 40, a slit 41a having a given width is formed to extend along the axial direction of the first detecting unit cover 224A. Each slit 41a has fitted therein the extension portion 32 of the projection member 231. The extension portion 32 is fitted in the slit 41a so as to penetrate the slit 41a radially from the inside to the outside of the peripheral wall 40. In the peripheral wall 40 of the first detecting unit cover 224A, a pressing groove 35 is formed in the vicinity of each slit 41a. Each pressing groove 35 is formed by cutting the inner peripheral surface of the peripheral wall 40 flat. Each pressing groove 35 has fitted therein a part of the flange portion 33 of the projection member 131. The depth of each pressing groove 35 (the depth in the radial direction of the peripheral wall 40) is set such that, when a part of the flange portion 33 is fitted in the pressing groove 35, the projection member 231 is pressed against the primary surface of the body portion 30 with a sufficient force.

In the peripheral wall 42 of the second detecting unit cover 224B, the edge portion on the proximal side (the side facing the first detecting unit cover 224A) has four shielding walls 43 formed integrally with the peripheral wall 42. The shielding walls 43 project from the peripheral wall 42 in the axial direction. The shielding walls 43 have a substantially rectangular shape. The four shielding walls 43 are arranged at regular intervals in the circumferential direction of the peripheral wall 42. The four shielding walls 43 are inserted in the four cutouts 41, respectively. The shielding walls 43 close the cutouts 41. At the extension end of each shielding wall 43, the surface facing the body portion 30 of the electrode 151a, 151b is partly thinned. The thinned portion of the shielding wall 43 receives a part of the remainder of the flange portion 33.

The following is an example of way of fixing the projection member 231 of each of the electrodes 151a, 151b to the primary surface of the associated body portion 30 (permanent magnet 3) in a contacting manner. The first detecting unit cover 224A and the body portions 30 (permanent magnets 3) of the electrodes 151a, 151b are previously mounted to the outer peripheral surface of the distal end side of the support block 17. Next, each of the extension portions 32 of the projection members 231 is fitted into the slit 41a of the first detecting unit cover 224A, and a part of the flange 33 is fitted into the pressing groove 35 of the peripheral wall 40. At this time, the part of the flange portion 33 of the projection member 231 is pressed radially inward by the inner surface of the pressing groove 35. Thus, the proximal end portion (flange portion 33) of the projection member 231 is pressed against the body portion 30 (permanent magnet 3). As a result, the projection member 231 is fixed, in a contacting manner, to the primary surface of the body portion 30 (permanent magnet 3) in an upright position.

Subsequently, the second detecting unit cover 224B is mounted to the outer peripheral surface of the distal end portion of the support block 17, such that the shielding walls 43 of the second detecting unit cover 224B are inserted into the associated cutouts 41 of the first detecting unit cover 224A. At this time, a part of the remainder of the flange portion 33 of each projection member 231 is received in the thinned portion of the peripheral wall 42 of the second detecting unit cover 224B. Subsequently, the second detecting unit cover 224B is fixed to the support block 17 by an appropriate means such as locking with a metal locking piece 45 (see FIG. 8).

Advantageous Effects of Third Embodiment

As described above, the conductive particle detecting device 214 of the embodiment, which is basically configured in the same manner as in the second embodiment, can produce substantially the same basic effects as the conductive particle detecting device 114 of the second embodiment.

In the conductive particle detecting device 214 of the embodiment, the projection members 231 projecting outward from the body portions 30 (permanent magnets 3) of the electrodes 151a, 151b are pressed radially inward by the pressing grooves 35 of the first detecting unit cover 224A. Thus, the projection members 231 are pressed against the body portions 30 of the electrodes 151a, 151b. Therefore, with the conductive particle detecting device 214 of the embodiment, it can be inhibited by a simple configuration that the contact between the body portions 30 and the projection members 231 falls instable, causing a drop in the voltage between the projection members 231 of the electrodes 151a, 151b adjacent to each other.

Configuration of Fourth Embodiment

Figure 9:
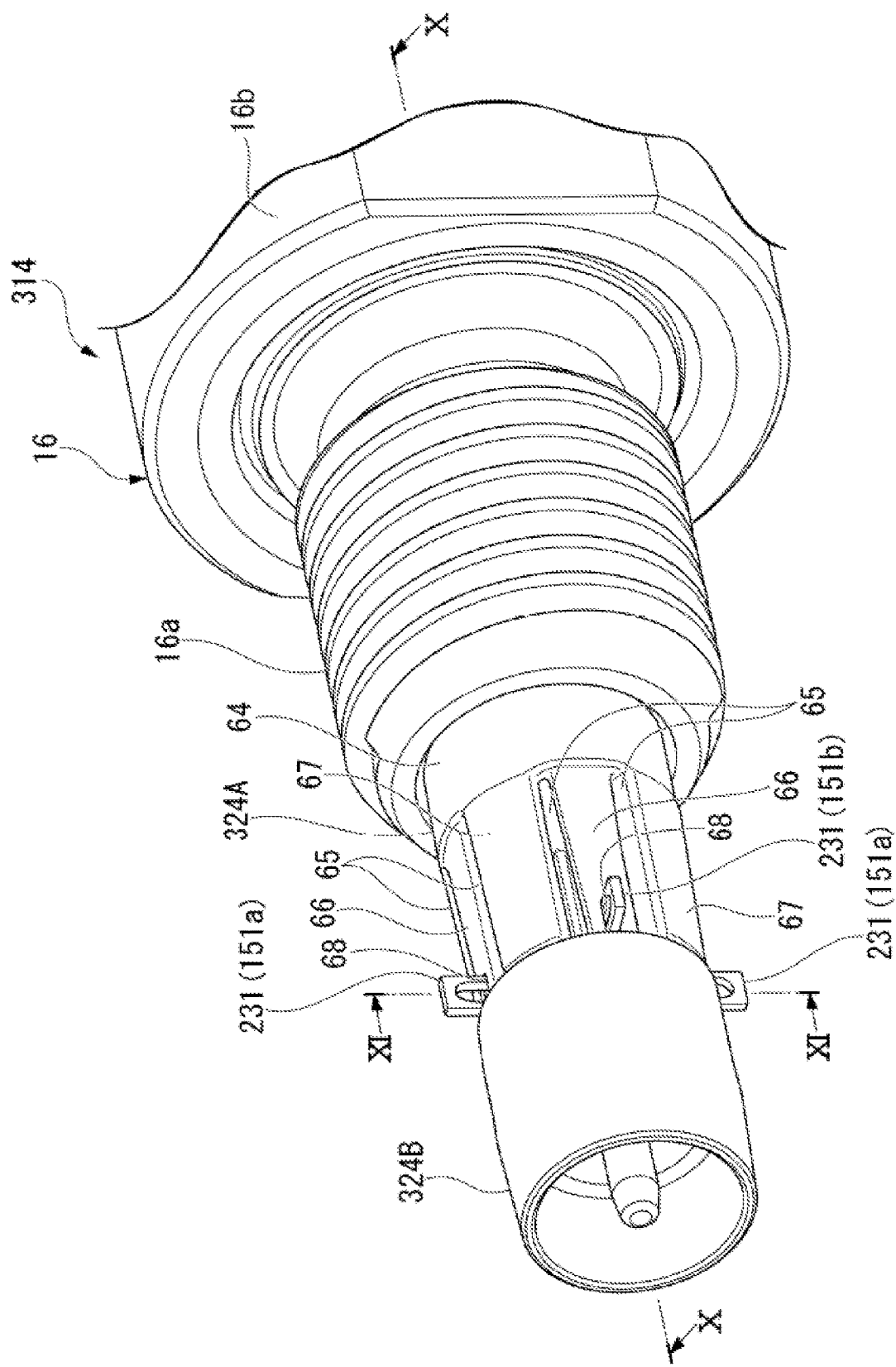
FIG. 9 is a perspective view showing a conductive particle detecting device according to a fourth embodiment.
Figure 10:
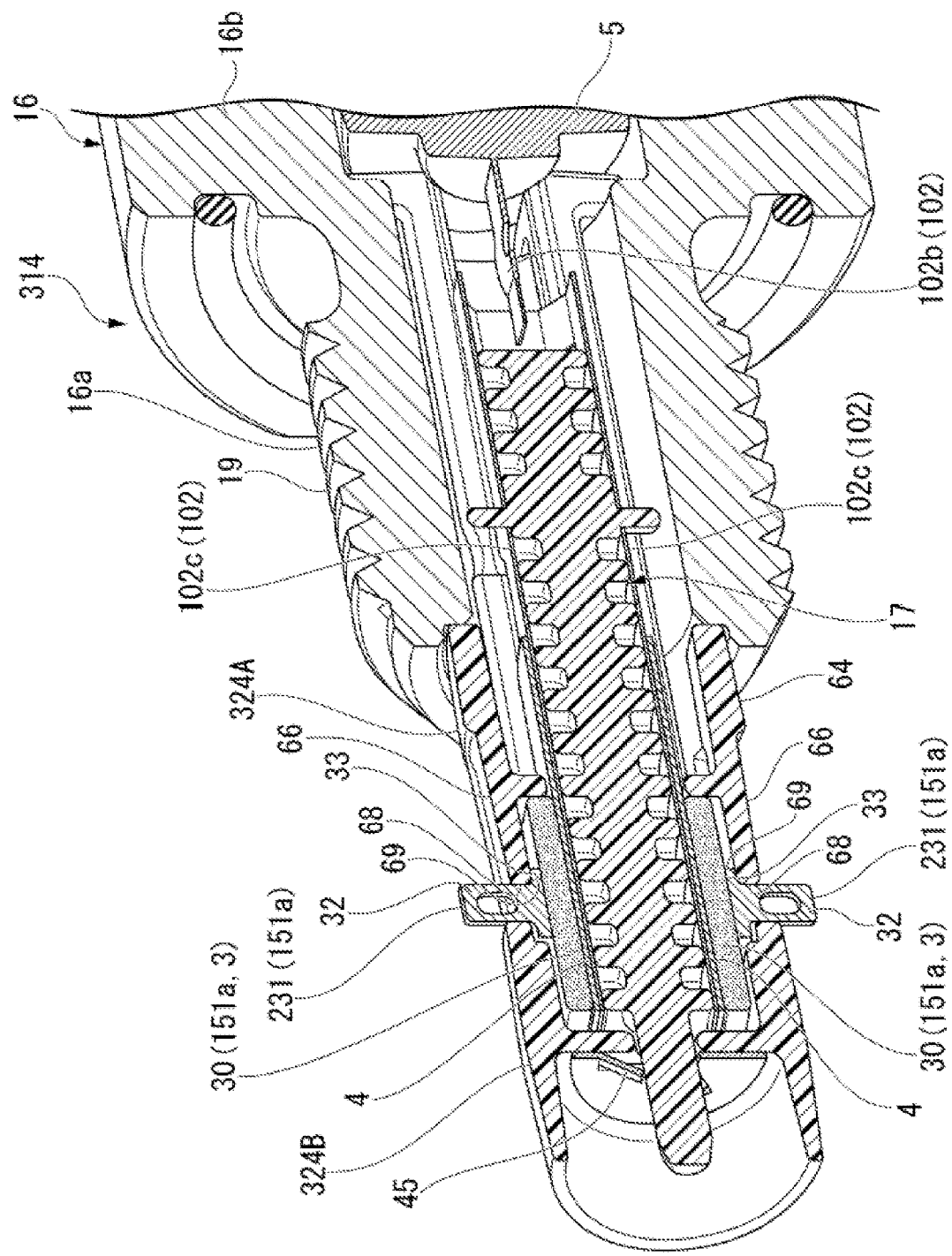
FIG. 10 is a partial sectional perspective view showing the conductive particle detecting device of FIG. 9 cut along the line X-X in FIG. 9.
Figure 11:
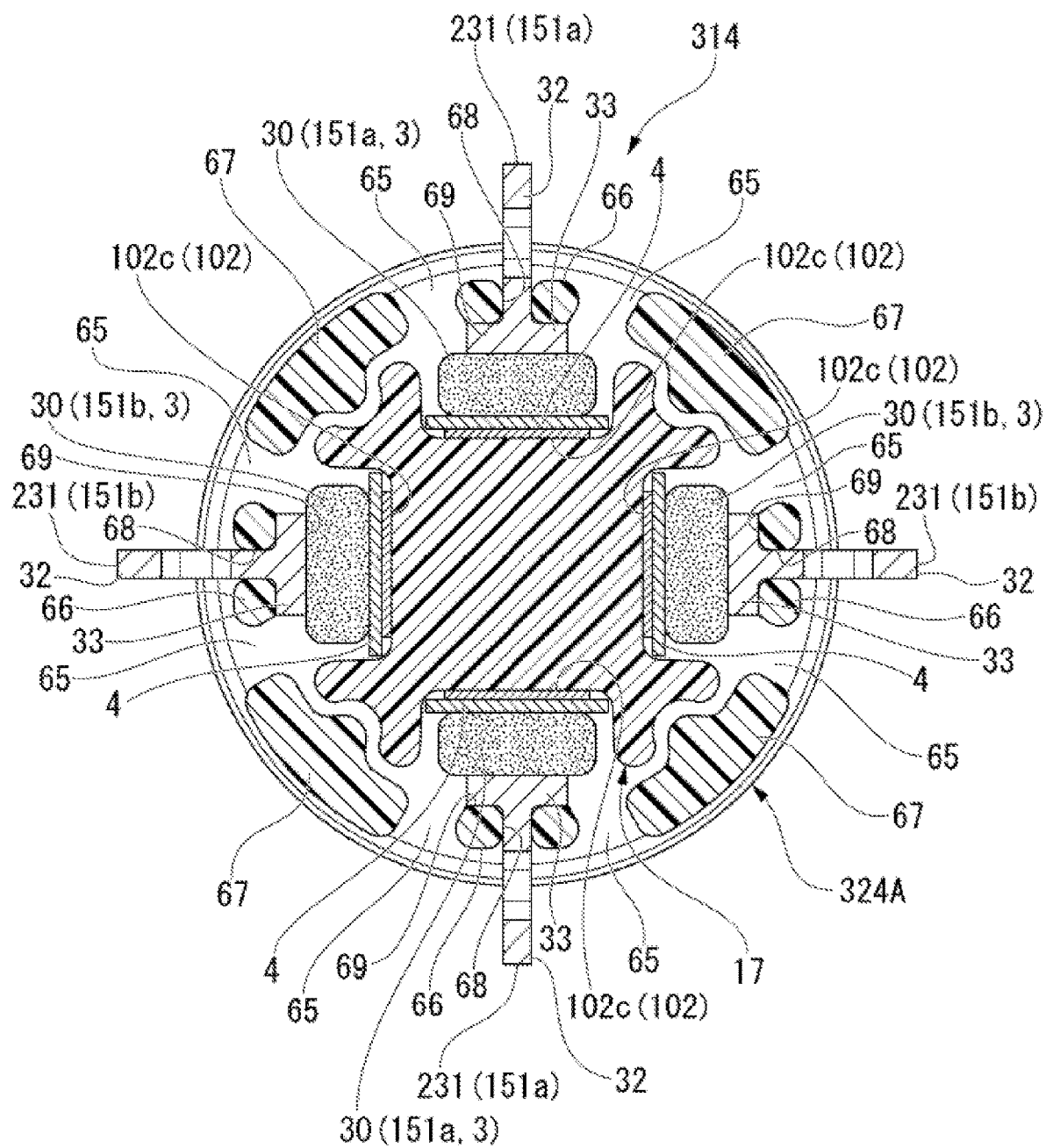
FIG. 11 is a sectional view showing the conductive particle detecting device of FIG. 9 along the line XI-XI in FIG. 9.

FIG. 9 is a perspective view showing a conductive particle detecting device 314 according to the present embodiment. FIG. 10 is a partial sectional perspective view showing the conductive particle detecting device 314 of FIG. 9 cut along the line X-X. FIG. 11 is a sectional view showing the conductive particle detecting device 314 along the line XI-XI in FIG. 9. The conductive particle detecting device 314 of the embodiment is basically configured in substantially the same manner as in the third embodiment. In the conductive particle detecting device 314 of the embodiment, the major difference from the third embodiment is the structure of a first detecting unit cover 324A and a second detecting unit cover 324B and, in particular, the structure of a locking portion for locking the projection members 231 (projection portions) of the electrodes 151a, 151b.

As in the third embodiment, each of the electrodes 151a, 151b has the body portion 30 and the projection member 231 (projection portion). The projection member 231 is formed of a conductive non-magnetic material such as brass, aluminum, or copper. The projection member 231 includes the extension portion 32 and the flange portion 33.

Both the first detecting unit cover 324A and the second detecting unit cover 324B have a substantially cylindrical shape and are mounted to the support block 17 so as to cover the outer periphery of the support block 17. The peripheral wall of the first detecting unit cover 324A has eight dividing slits 65 formed therein. The dividing slits 65 are arranged at intervals in the circumferential direction of the peripheral wall Each of the dividing slits 65 extends along the axial direction of the first detecting unit cover 324A. The first detecting unit cover 324A includes a cylindrical portion 64 formed in the proximal portion thereof (the end portion facing away from the second detecting unit cover 324B). The end of each dividing slit 65 is open toward the distal end side of the first detecting unit cover 324A (the side proximate to the second detecting unit cover 324B). The eight dividing slits 65 divide the region of the peripheral wall of the first detecting unit cover 324A other than the cylindrical portion 64 into eight strips extending in the axial direction. Four of the eight strips constitute locking pieces 66. The locking pieces 66 lock the projection members 231 of the electrodes 151a, 151b. The remaining four strips out of the eight strips constitute cover pieces 67. The cover pieces 67 cover the outside of the support block 17, instead of locking the projection members 231. The locking pieces 66 and the cover pieces 67 alternate in the outer periphery of the first detecting unit cover 324A. In the circumferential direction around the support block 17, the locking pieces 66 are positioned to substantially overlap the four permanent magnets 3 (the four body portions 30 of the electrodes 151a, 151b) on the support block 17.

The four cover pieces 67 have a substantially arc-shaped section having substantially the same diameter (substantially the same inner and outer diameters) as the cylindrical portion 64. The four locking pieces 66 have a flat plate-shaped section. The locking pieces 66 have a smaller thickness than the cover pieces 67. In the distal end surface of each locking pieces 66, a slit 68 having a given width is formed to extend along the axial direction of the first detecting unit cover 324A.

The slit 68 of each locking piece 66 has fitted therein the extension portion 32 of the projection member 231. The extension portion 32 is fitted in the slit 68 so as to penetrate the slit 68 radially from the inside to the outside of the locking piece 66. The back surface of the distal end portion of the locking piece 66 forms a pressing surface 69 for pressing a part of the flange portion 33 of the projection member 231. When the extension portion 32 of the projection member 231 is fitted into the slit 68, the pressing surface 69 presses the part of the flange portion 33 against the primary surface of the body portion 30 of the electrode 151a, 151b.

The gap between the back surface (pressing surface 69) of the locking piece 66 and the primary surface of the body portion 30 is smaller than the thickness of the flange portion 33. When the extension portion 32 of the projection member 231 is pressed into the slit 68 of the locking piece 66, the entirety of the locking piece 66 is elastically deformed in the thickness direction thereof, so as to allow the flange portion 33 to be inserted into the gap between the locking piece 66 and the body portion 30.

In the peripheral wall of the second detecting unit cover 324B, the edge portion on the proximal side (the side facing the first detecting unit cover 224A) has a surface facing the body portion 30, and this surface is partly thinned. The thinned portion of the second detecting unit cover 324B receives a part of the remainder of the flange portion 33.

The following is a way of fixing the projection member 231 of each of the electrodes 151a, 151b to the primary surface of the associated body portion 30 (permanent magnet 3) in a contacting manner. The first detecting unit cover 324A and the body portions 30 (permanent magnets 3) of the electrodes 151a, 151b are mounted to the outer peripheral surface of the distal end portion of the support block 17. In this state, each extension portion 32 is fitted into the slit of the locking piece 66, and a part of the flange portion 33 is fitted into the gap between the pressing surface 69 of the locking piece 66 and the body portion of the electrode 151a, 151b. At this time, the locking piece 66 is elastically deformed in the thickness direction thereof. As a result, the part of the flange portion 33 is pressed radially inward by the pressing surface 69, and the proximal end (flange portion 33) of the projection member 231 is pressed against the body portion 30 (permanent magnet 3). The projection member 231 is fixed, in a contacting manner, to the outer surface of the body portion 30 (permanent magnet 3) in an upright position.

Subsequently, the second detecting unit cover 324B is mounted to the outer peripheral surface of the distal end portion of the support block 17. At this time, a part of the remainder of the flange portion 33 of each projection member 231 is received in the thinned portion of the second detecting unit cover 324B. Subsequently, the second detecting unit cover 324B is fixed to the support block 17 by an appropriate means such as locking with a metal locking piece 45.

Advantageous Effects of Fourth Embodiment

As described above, the conductive particle detecting device 314 of the embodiment, which is basically configured in the same manner as in the third embodiment, can produce substantially the same basic effects as the conductive particle detecting device 214 of the third embodiment.

In the conductive particle detecting device 314 of the embodiment, the first detecting unit cover 324A includes the locking pieces 66 extending in the axial direction. Each of the locking pieces 66 has the slit 68 and the pressing surface 69 for supporting the projection member 231. Therefore, when the projection member 231 is nipped for fixation between the first detecting unit cover 324A and the body portion 30, the locking piece 66 is elastically deformed in the thickness direction thereof, thereby facilitating the fixing work. In fixing the projection member 231, unwanted strain can be prevented from occurring in a part of the first detecting unit cover 324A.

The present disclosure is not limited to the above-described embodiments and can be modified in a variety of designs without deviating from the spirit of the present disclosure. For example, although the conductive particle detecting devices of the above embodiments are applied to a speed reducer for reducing the rotational speed of a drive source, the mechanical devices to which the conductive particle detecting devices are applied are not limited to speed reducers, but may also be any other mechanical devices not including a speed reducing mechanism if a mechanical mechanism is housed in a casing. Although the conductive particle detecting devices of the above embodiments detect metal powder produced in the mechanical device, conductive particles other than metals can also be detected when at least a part of the mechanical mechanism of the mechanical device is formed of a conductive material other than metals. In the above embodiments, the target metal powder (conductive particles) is metal powder (conductive particles) having a particle size of 10 μm or larger. It is also possible that the target metal powder (conductive particles) is metal powder (conductive particles) having a particle size of 20 μm or larger. In this case, the attractive force of the permanent magnets is set such that the lubricant remains as a non-conductive layer around the metal powder (conductive particles) having a particle size of less than 20 μm. In this way, conductive particles produced from the mechanical device having any particle size can be detected as a detection target by varying the attractive force of the permanent magnets.

LIST OF REFERENCE NUMBERS 3 permanent magnet
10 speed reducer (mechanical device)
11 speed reducing mechanism unit (mechanism)
12 casing
13 lubricant
14, 114, 214, 314 conductive particle detecting device
30 body portion
31, 131, 231 projection member (projection portion)
50 detecting circuit
51a, 51b, 151a, 151b electrode
224A, 324A first detecting unit cover (detecting unit cover)

What is claimed is:
1. A conductive particle detecting device, comprising:
a plurality of electrodes arranged at intervals in a non-conductive lubricant;
a permanent magnet for accumulating conductive particles between adjacent ones of the plurality of electrodes by a magnetic force, the conductive particles being a detection target mixing into the lubricant; and
a detecting circuit for detecting the conductive particles based on electrical resistance between the adjacent ones of the plurality of electrodes,
wherein an attractive force of the permanent magnet is set such that the lubricant remains as a non-conductive layer around fine particles having electrical conductivity and having a smaller particle size than the conductive particles, wherein each of the plurality of electrodes has a primary surface to which the fine particles are adhered, and wherein each of the plurality of electrodes includes a projection portion having electrical conductivity and partly projecting from the primary surface.

2. The conductive particle detecting device of claim 1, wherein the conductive particles have a particle size of 10 μm or larger, and wherein the fine particles have a particle size of less than 10 μm.

3. The conductive particle detecting device of claim 2, wherein the fine particles have a particle size of less than 2 μm.

4. The conductive particle detecting device of claim 1, wherein the projection portion includes a conductive non-magnetic material.

5. The conductive particle detecting device of claim 1, wherein the magnetic force of the permanent magnet is set such that the fine particles adhered to each of the plurality of electrodes reach saturation within a range in which the fine particles do not entirely cover the projection portion, and the fine particles are dispersed in the lubricant.

6. The conductive particle detecting device of claim 5, wherein the magnetic force of the permanent magnet is set such that, in a mechanical device that produces a largest amount of conductive particles among a plurality of types of mechanical devices to which the conductive particle detecting device is applied, the fine particles adhered to each of the plurality of electrodes reach saturation within a range in which the fine particles do not entirely cover the projection portion, and the fine particles are dispersed in the lubricant.

7. The conductive particle detecting device of claim 1, wherein each of the plurality of electrodes includes:
a body portion; and
a projection member formed separately from the body portion and constituting the projection portion, and
wherein the projection member is pressed against the body portion by a detecting unit cover that covers a circumference of the body portion.

8. A conductive particle detecting device, comprising:
a plurality of permanent magnets having electrical conductivity arranged at intervals in a non-conductive lubricant; and
a detecting circuit for detecting electrical resistance between electrodes different from each other, adjacent ones of the plurality of permanent magnets being defined as the electrodes different from each other,
wherein conductive particles mixing into the lubricant are defined as a detection target, and particles having electrical conductivity and having a smaller particle size than the conductive particles are defined as fine particles, and
wherein a part of the fine particles between the electrodes is maintained out of contact with the electrodes such that upon application of electric current, the fine particles do not conduct electricity to the electrodes, wherein each of the plurality of electrodes has a primary surface to which the fine particles are adhered, and wherein each of the plurality of electrodes includes a projection portion having electrical conductivity and partly projecting from the primary surface.

9. A conductive particle detecting device, comprising:
a plurality of electrodes arranged at intervals in a non-conductive lubricant;
a detecting circuit for detecting conductive particles based on electrical resistance between the plurality of electrodes, the conductive particles being a detection target mixing into the lubricant,
wherein particles having electrical conductivity and having a smaller particle size than the conductive particles are defined as fine particles, and
wherein upon application of electric current, the fine particles do not conduct electricity to the plurality of electrodes, wherein each of the plurality of electrodes has a primary surface to which the fine particles are adhered, and wherein each of the plurality of electrodes includes a projection portion having electrical conductivity and partly projecting from the primary surface.

10. A mechanical device, comprising:
a mechanical mechanism;
a casing containing the mechanism and a non-conductive lubricant; and
a conductive particle detecting device for detecting conductive particles, the conductive particles being a detection target mixing into the lubricant,
wherein the conductive particle detecting device includes:
a plurality of electrodes arranged at intervals in the lubricant;
a permanent magnet for accumulating the conductive particles between adjacent ones of the plurality of electrodes by a magnetic force; and
a detecting circuit for detecting the conductive particles based on electrical resistance between the adjacent ones of the plurality of electrodes,
wherein an attractive force of the permanent magnet is set such that upon application of electric current, fine particles having electrical conductivity and having a smaller particle size than the conductive particles do not conduct electricity to the plurality of electrodes, wherein each of the plurality of electrodes has a primary surface to which the fine particles are adhered, and wherein each of the plurality of electrodes includes a projection portion having electrical conductivity and partly projecting from the primary surface.

\* \* \* \* \*